United States Patent
Soffer et al.

(10) Patent No.: US 11,253,158 B2
(45) Date of Patent: Feb. 22, 2022

(54) INFRARED THERMOGRAPHY PLATFORM FOR DETERMINING VASCULAR HEALTH OF INDIVIDUALS

(71) Applicant: THERMWORX, LLC, Aventura, FL (US)

(72) Inventors: Ariel D. Soffer, Aventura, FL (US); David Wright, Oxfordshire (GB)

(73) Assignee: USA THERM, INC., Aventura, FL (US)

( * ) Notice: Subject to any disclaimer, the term of this patent is extended or adjusted under 35 U.S.C. 154(b) by 388 days.

(21) Appl. No.: 16/421,721

(22) Filed: May 24, 2019

(65) Prior Publication Data

US 2019/0365241 A1    Dec. 5, 2019

Related U.S. Application Data

(60) Provisional application No. 62/677,887, filed on May 30, 2018.

(51) Int. Cl.
*A61B 5/01* (2006.01)
*A61B 5/00* (2006.01)
(Continued)

(52) U.S. Cl.
CPC ............ *A61B 5/015* (2013.01); *A61B 5/0075* (2013.01); *A61B 5/0082* (2013.01); *A61B 5/742* (2013.01);
(Continued)

(58) Field of Classification Search
CPC ....... A61B 5/015; A61B 5/0082; A61B 5/742; A61B 5/0075; A61B 5/02007;
(Continued)

(56) References Cited

U.S. PATENT DOCUMENTS

2004/0073132 A1   4/2004 Maahs et al.
2005/0043969 A1*  2/2005 Sarel ..................... G16H 80/00
                                                        705/2

(Continued)

FOREIGN PATENT DOCUMENTS

WO   WO2018002863    1/2018
WO   WO2018002925    1/2018

OTHER PUBLICATIONS

Lin et al. 2017 Journal of Vascular Surgery Cases and Innovative Techniques 3:205-208; (Year: 2017).*
Kockara et al. 2014 IEEE Innovations in Technology Conference 2014 p. 1-5 (Year: 2014).*
Cholewka et al. 2017 J.Therm.Anal.Calorim. 130:1317-1326; (Year: 2017).*

*Primary Examiner* — Keith M Raymond
*Assistant Examiner* — Patrick M Mehl
(74) *Attorney, Agent, or Firm* — Allen, Dyer, Doppelt + Gilchrist, PA (57) ABSTRACT

A vascular thermography system includes a portable electronic device and a thermal image analyzer in communications therewith. The portable electronic device includes a thermal imager to generate a thermal image of an anatomical area of a patient, a display, a processor configured to display the thermal image on the display, and a transceiver coupled to the processor to transmit the thermal image. The thermal image analyzer receives the thermal image from the portable electronic device, determines an assessment on vascular health of the patient based on comparing the thermal image to a database of thermal images, and transmits the assessment to the portable electronic device.

20 Claims, 8 Drawing Sheets

(51) Int. Cl.
*G06T 7/00* (2017.01)
*G16H 30/20* (2018.01)
*G16H 30/40* (2018.01)
*A61B 5/02* (2006.01)

(52) U.S. Cl.
CPC .......... *G06T 7/0012* (2013.01); *G06T 7/0014* (2013.01); *G16H 30/20* (2018.01); *G16H 30/40* (2018.01); *A61B 5/02007* (2013.01); *G06T 2207/10048* (2013.01); *G06T 2207/30004* (2013.01); *G06T 2207/30088* (2013.01); *G06T 2207/30101* (2013.01); *G06T 2210/41* (2013.01)

(58) Field of Classification Search
CPC ........ A61B 8/0891; A61B 8/06; G16H 30/40; G16H 30/20; G06T 7/0014; G06T 7/0012; G06T 2207/10048; G06T 2207/30088; G06T 2210/41; G06T 2207/30101; G06T 2207/30004
See application file for complete search history.

(56) References Cited

U.S. PATENT DOCUMENTS

| | | | |
|---|---|---|---|
| 2010/0191541 A1* | 7/2010 | Prokoski | A61B 5/418 705/2 |
| 2011/0032326 A1* | 2/2011 | Hollander | H04N 1/0044 348/36 |
| 2013/0116573 A1 | 5/2013 | Herman | |
| 2014/0112537 A1* | 4/2014 | Frank | G01V 8/10 382/103 |
| 2014/0164968 A1* | 6/2014 | Aalami | G16H 40/63 715/771 |
| 2015/0257651 A1* | 9/2015 | Angott | A61B 5/4312 600/474 |
| 2016/0259889 A1* | 9/2016 | Murtha | G06T 13/40 |
| 2017/0027450 A1* | 2/2017 | Toledano | A61B 5/0077 |
| 2017/0277831 A1* | 9/2017 | Ruff | A61B 6/485 |
| 2018/0005085 A1* | 1/2018 | Kakileti | G06K 9/6267 |
| 2018/0098727 A1* | 4/2018 | Spahn | G01J 5/0025 |

\* cited by examiner

INFRARED THERMOGRAPHY PLATFORM FOR DETERMINING VASCULAR HEALTH OF INDIVIDUALS

RELATED APPLICATIONS

This application claims the benefit of provisional application Ser. No. 62/667,887 filed May 30, 2018, which is hereby incorporated herein in its entirety by reference.

TECHNICAL FIELD

The present disclosure relates to vascular medicine, and more particularly, to the use of infrared thermography for determining the vascular health of individuals.

BACKGROUND

Venous insufficiency is a common condition that manifests itself in a very broad range from invisible vein incompetence to massive varicose veins and ultimately ulcers. In excess of 40% of the adult population are affected to some extent.

Improper functioning of the vein valves in the leg, for example, can cause swelling and skin changes. Normally, the vein valves keep blood moving back toward the heart. Venous valvular failure leads to a reverse blood flow in the veins. In addition to swelling or skin color changes, varicose veins may form. If the condition progresses, leg ulcers may form. Treatment includes compression stockings, surgery, foam sclerotherapy, heat ablation and glue closure, for example.

If not treated, the pressure and swelling may increase until the tiniest blood vessels in the legs (capillaries) burst. When this happens, the overlying skin takes on a reddish-brown color and is very sensitive to being broken if bumped or scratched.

Tests called a venogram or a duplex ultrasound may be used to examine the blood circulation in a patient. During a venogram, an intravenous (IV) x-ray contrast solution is placed into the veins. The contrast solution causes the blood vessels to appear white on the X-ray image, which helps the doctor see them on the image. The contrast will provide a clear X-ray picture of the blood vessels which would otherwise be invisible.

The duplex ultrasound may be used to identify the veins and arteries and test the speed and direction of blood flow in the veins. A technician will place gel on the skin of the patient and then press a small hand-held device (transducer) against the skin. The transducer sends sound waves that bounce back off tissues and vessels to the transducer. The sound waves are analyzed, and an image of the vessel is created and displayed on a monitor.

Even in view of the current tests used to examine blood flow circulation, there is still a need for a non-invasive and straightforward screening methodology to assess the vascular health of individuals.

SUMMARY

A vascular thermography system includes at least one portable electronic device and a thermal image analyzer in communications therewith. The portable electronic device includes a thermal imager configured to generate a thermal image of an anatomical area of a patient, a display, a processor configured to display the thermal image on the display, and a transceiver coupled to the processor and configured to transmit the thermal image. The thermal image analyzer is configured to receive the thermal image from the portable electronic device, determine an assessment on vascular health of the patient based on comparing the thermal image to a database of thermal images, and transmit the assessment to the portable electronic device.

The vascular thermography system advantageously allows for real-time clinical assessments on the vascular health of patients. By using thermography and an intelligent database this allows for real-time clinical assessments to be performed non-invasively and without requiring expensive ultrasound equipment.

The vascular thermography system may further comprising a remote storage device associated with the thermal image analyzer. The remote storage device may be configured to store a patient list and cataloged thermal images of patients on the patient list. The processor may be further configured to execute a clinical thermography application to display a login screen, and display vein scan settings based on a user of the portable electronic device logging in. The vein scan settings include at least one of a live view setting allowing the user to immediately examine a patient, a new patient setting for the user to add a new patient to the patient list, and an existing patient setting for the user to retrieve an existing patient from the patient list.

The processor may be further configured to display a drop down list so the user can label the anatomical area being displayed in the thermal image, and store the labeled thermal image in the cataloged thermal images at the remote storage device, based on execution of the clinical thermography application.

The thermal image analyzer and the remote storage device may be cloud-based. Communications between the portable electronic device and both the thermal image analyzer and the remote storage device may be encrypted so as to be HIPPA (Health Insurance Portability and Accountability) compliant.

The database of thermal images may comprise a plurality of thermal patterns corresponding to a range of vascular health conditions, and wherein the thermal image analyzer may be further configured to compare a thermal pattern within the thermal image to the plurality of thermal patterns in the database of thermal images. The assessment on vascular health of the patient may include statistical probabilities of certain disease states based on the thermal pattern within the thermal image.

The thermal image analyzer may be further configured to use machine learning to determine the assessment on vascular health of the patient.

The portable electronic device may further comprise an external interface coupled to the processor, and a housing. The housing is configured to carry the display, the processor, the transceiver, and the external interface. The thermal imager may be external the housing and removeably coupled to the external interface.

The portable electronic device may further comprises a camera configured to take a photograph of the same anatomical area as being displayed in the thermal image. The processor may be further configured to display in a side-by-side comparison the thermal image and the photograph of the same anatomical area.

Another aspect is directed to a vascular thermography system that includes at least one portable electronic device comprising a thermal imager configured to generate a thermal image of an anatomical area of a patient, a display, a transceiver, and a processor coupled to the thermal imager, the display, and the transceiver. The processor may be configured to execute a clinical thermography application to display the thermal image, display a drop down list so the user can label the anatomical area being displayed in the thermal image, and transmit the labeled thermal image. The vascular thermography system may further include a remote storage device configured to store the labeled thermal image as a cataloged thermal image of the patient, and a thermal image analyzer associated with the remote storage device. The thermal image analyzer may be configured to receive the cataloged thermal image from the remote storage device, determine an assessment on vascular health of the patient based on comparing the cataloged thermal image to a database of thermal images, and transmit the assessment to the at least one portable electronic device.

Yet another aspect is directed to a method for operating a vascular thermography system comprising at least one portable electronic device and a thermal image analyzer. The portable electronic device includes a thermal imager, a display, a transceiver, and a processor coupled to the thermal imager, the display, and the transceiver. The method comprises operating the at least one portable electronic device to generate a thermal image of an anatomical area of a patient for display, and transmit the thermal image to the thermal image analyzer. The method further includes operating the thermal image analyzer may be operated to receive the thermal image from the at least one portable electronic device, determine an assessment on vascular health of the patient based on comparing the thermal image to a database of thermal images, and transmit the assessment to the at least one portable electronic device.

DETAILED DESCRIPTION

The present description is made with reference to the accompanying drawings, in which exemplary embodiments are shown. However, many different embodiments may be used, and thus the description should not be construed as limited to the particular embodiments set forth herein. Rather, these embodiments are provided so that this disclosure will be thorough and complete. Like numbers refer to like elements throughout.

Infrared thermography platforms as described below for determining vascular health of individuals may be configured for clinical use or for retail use. Clinical use of an infrared thermography platform involves a doctor operating a portable vascular thermography device that is in communications with a cloud based thermal image analyzer to assess the vascular health of a patient. Retail use of an infrared thermography platform involves an individual interacting with a kiosk to assess the vascular health of a customer so as to recommend appropriately sized and strength of compression socks as necessary.

Figure 1:
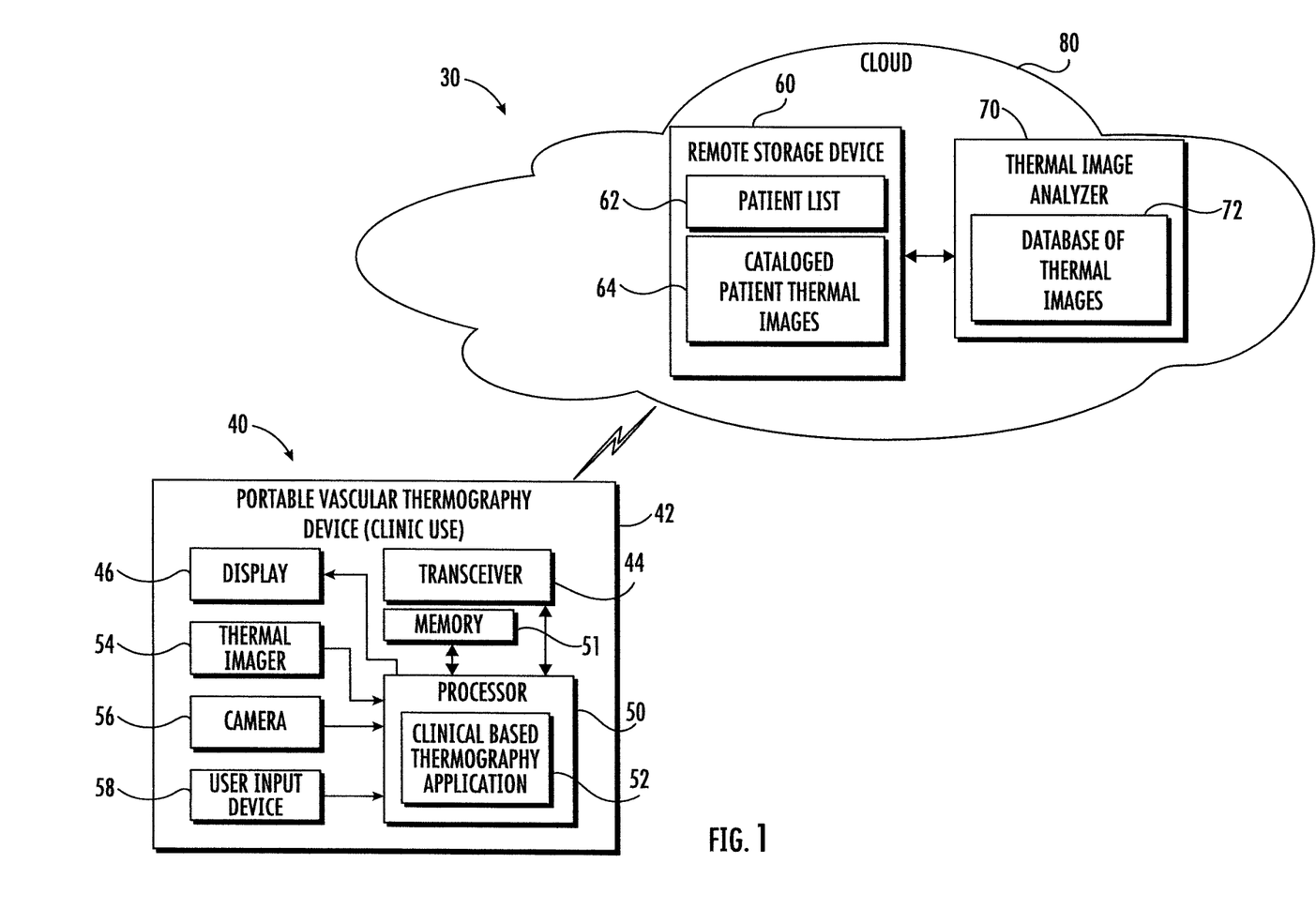
FIG. 1 is a block diagram of a clinical based infrared thermography system in accordance with the disclosure.

Referring initially to FIG. 1, a clinical based infrared thermography system 30 includes at least one portable vascular thermography device 40 operating a clinical based thermography application 50 in communications with a remote storage device 60 and a thermal image analyzer 70. The portable vascular thermography device 40 may also be referred to as a portable electronic device, and the clinical based infrared thermography system 30 may also be referred to as a vascular thermography system 30. The vascular thermography system 30 advantageously allows for real-time clinical assessments on the vascular health of individuals. By using thermography and an intelligent database this allows for real-time clinical assessments to be performed non-invasively and without requiring expensive ultrasound equipment.

As readily appreciated by those skilled in the art, infrared clinical thermography is a passive non-contact, and non-invasive method for mapping surface temperatures of the body. The differential of relative skin temperatures can be utilized to map and thus detect many abnormalities not seen by other diagnostic tools nor the human eye. The portable vascular thermography device 40 coupled with a validated database of thermal images 72 provides diagnostic immediacy that will enable physicians, nurses, and even consumers to quickly know more about their vascular health.

The remote storage device 60 and the thermal image analyzer 70 are cloud based 80. In other embodiments, the remote storage device 60 and the thermal image analyzer 70 may be co-located with the portable vascular thermography device 40. Even though the remote storage device 60 and the thermal image analyzer 70 are shown as separate components, they may be combined into a single component.

Communications between the portable vascular thermography device 40 and the remote storage device 60 and the thermal image analyzer 70 are encrypted to be HIPPA (Health Insurance Portability and Accountability Act) complainant. To be HIPPA compliant, the clinical based infrared thermography system 30 includes encryption, an encrypted firewall, and role-based security to give users different levels of access based on their roles.

The remote storage device 60 is configured to store a patient list 62 and cataloged patient thermal images 64 as provided by the portable vascular thermography device 40. The thermal images are cataloged into corresponding labeled anatomical areas, such as left thigh, right calf, etc. The cataloging may be performed by the clinical based thermography application 50 or by the thermal image analyzer 70.

The thermal image analyzer 70 is coupled to the remote storage device 60 and is configured to provide diagnosis or an assessment of the cataloged patient thermal images 64 by comparing these images to the database of thermal images 72. The thermal image analyzer 70 may be configured to use machine learning to provide statistical probabilities of certain disease states based on the thermal patterns of the cataloged patient thermal images 64.

The portable vascular thermography device 40 includes a housing 42, a transceiver 44 carried by the housing 42 to communicate with the remote storage device 60 and the thermal image analyzer 70, and a display 46 carried by the housing 42.

The display 46 and the transceiver 44 are coupled to a processor 50 also carried by the housing 42. The processor 50 is configured to execute a clinical based thermography application 52.

A thermal imager 54 is carried by the housing 42 and is coupled to the processor 60. Optionally, the thermal imager 54 may be a separate component that is externally coupled to the portable vascular thermography device 40. A memory 51 is coupled to the processor 50 for storing thermal images prior to the thermal images being stored in the remote storage device 60.

In addition, a camera 56 may be carried by the housing 42 and coupled to the processor 60. The camera 56 allows for a comparison between a patient's thermal image and a standard photograph of the anatomical area being examined. A user input device 58 also carried by the housing 42 is coupled to the processor 50.

The portable vascular thermography device 40 may be configured as an iPhone, iPod, iPad or Android device, for example. If the portable vascular thermography device 40 is configured as an iPhone, for example, then the thermal imager 54 may be separate from the iPhone and coupled thereto via the iPhone's USB interface. An example external plug-in thermal imager 54 is FLIR ONE Gen 3 as provided by FLIR Systems, Inc.

Figure 2:
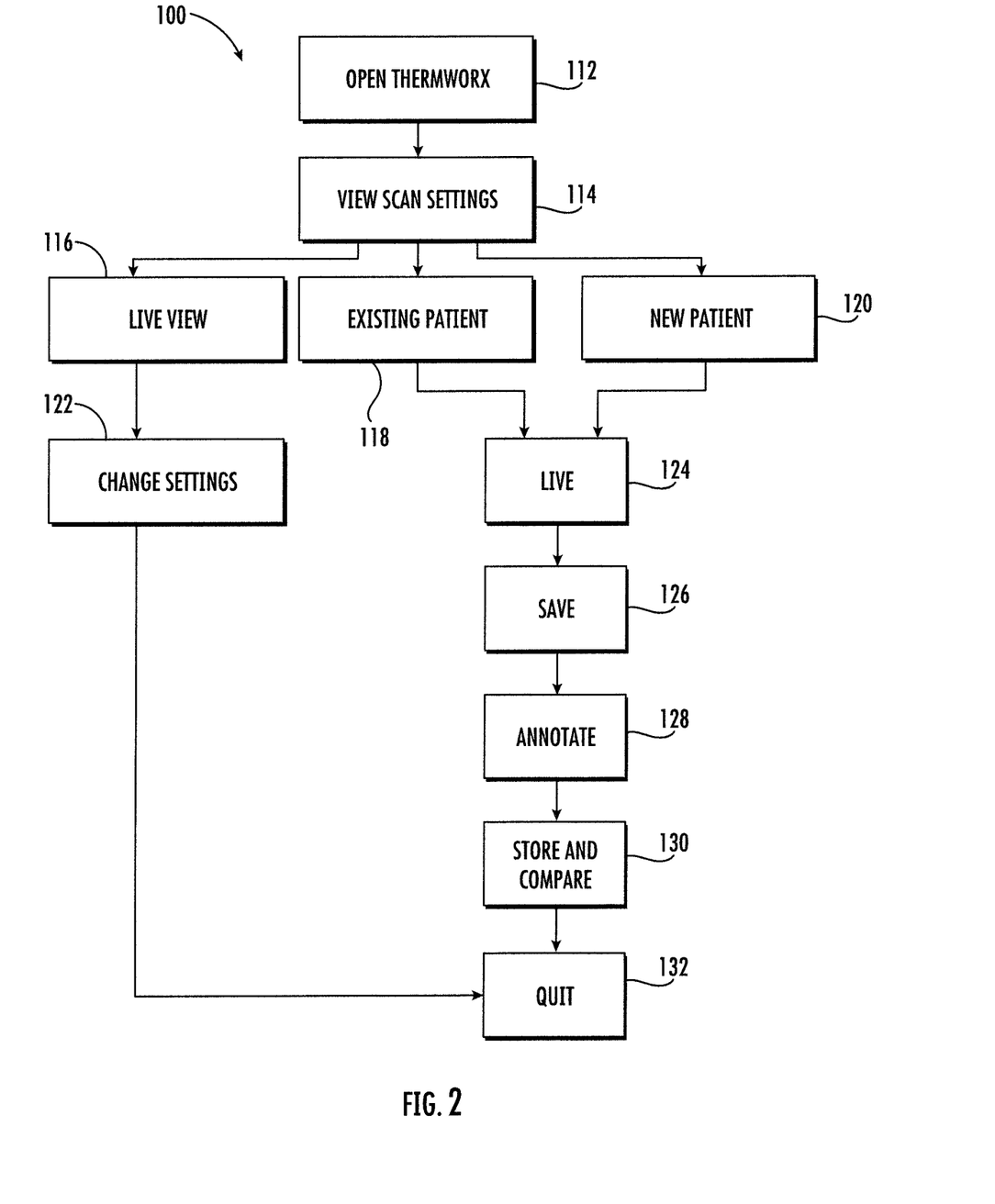
FIG. 2 is a flow diagram for operating the clinical based thermography application illustrated in FIG. 1.

Referring now to the flow diagram 100 in FIG. 2 and to the display screens in FIGS. 3-9, operation of the infrared thermography application 50 by a doctor will be discussed. The clinical based thermography application 50 may also be referred to as Thermworx.

Figure 3:
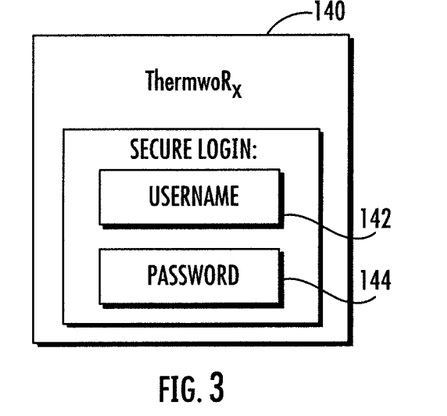
FIG. 3-9 are various display screens corresponding to the flow diagram illustrated in FIG. 2.
Figure 4:
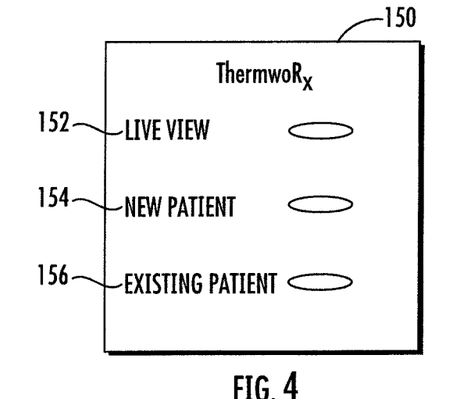

From the start, the clinical based infrared thermography application 50 is opened at Block 112 via a login screen 140 as shown in FIG. 3. The login screen 140 includes a username field 142 and a password field 144. At Block 114 the available vein scan settings are provided via display screen 150 as shown in FIG. 4. The vein scan settings include a live view setting 152, a new patient setting 154 and an existing patient setting 156.

The live view setting 152 allows the doctor to immediately examine a patient at Block 116 regardless of whether the patient is an existing patient or a new patient. As the setting names imply, the existing patient setting 156 is for selecting an existing patient at Block 118 from the remote storage device 60, and the new patient setting 154 is for entering a new patient at Block 120 into the remote storage device 60.

Figure 5:
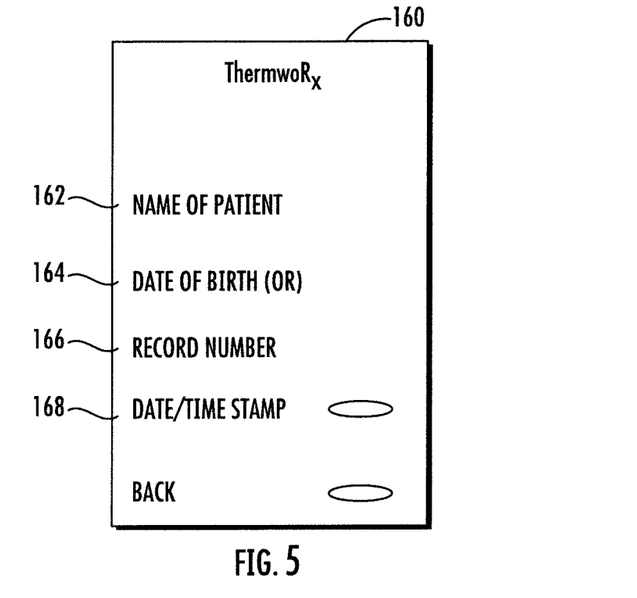

If the existing patient setting 156 is selected by the doctor, then display screen 160 appears as shown in FIG. 5. The doctor is to enter information into a name of patient field 162, a date of birth field 164 or a record number field 166, and a data/time stamp field 168.

Figure 6:
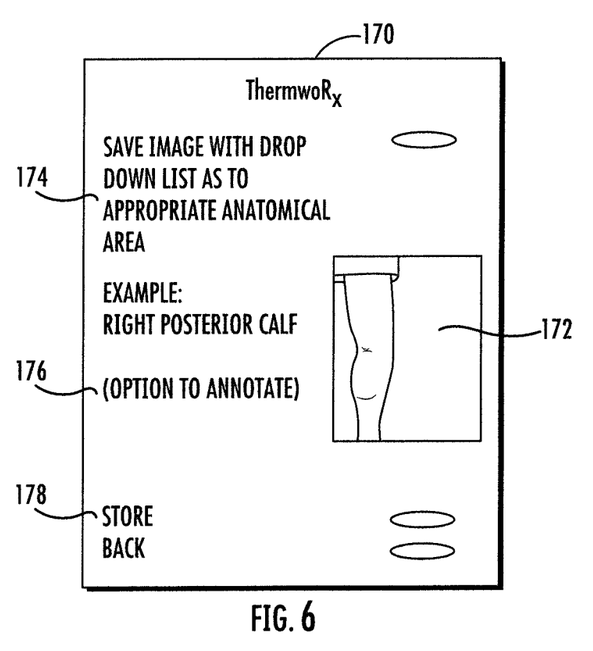

With the existing patient's information having been retrieved, the doctor may then use the thermal imager 54 to provide a thermal image 172 of the existing patient's right leg, for example, as shown in FIG. 6. The doctor has access to a save image field 174 for saving the thermal image 172. The thermal image 172 is saved within the memory 51 prior to being stored in the remote storage device 60.

Prior to the thermal image 172 being saved, the doctor selects from a drop down list to designate or label an appropriate anatomical area to the thermal image 172. In this case, the appropriate anatomical area is right posterior calf.

The doctor has an option to annotate the thermal image via the option to annotate field 176. If the doctor wants to store the annotated thermal image 172 within the remote storage device 60, then the store field 178 is selected. The annotated thermal image 172 is stored within the cataloged patient thermal images 64.

Referring back to the flow diagram 100, after an existing patient 118 or a new patient 120 has been selected, the following steps are the same. These steps include providing the live thermal image 172 of the area being examined at Block 124, saving the thermal image 172 corresponding to an appropriate anatomical area at Block 126, an option to annotate the thermal image 172 at Block 128, and storing the thermal image 172 within the remote storage device 60 at Block 130.

Figure 7:
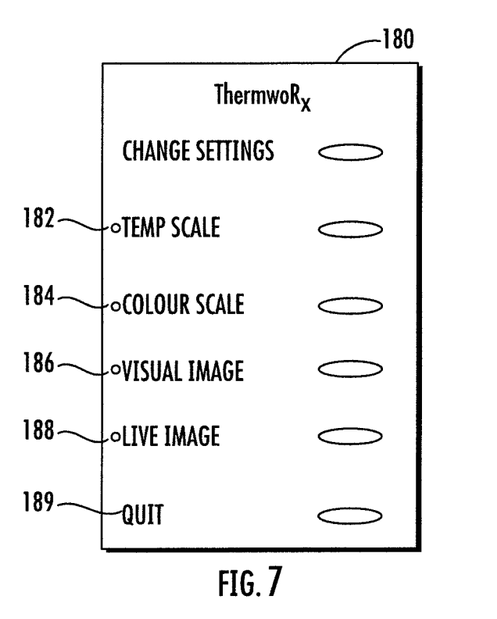

At Block 122 following the live view Block 116, the settings may be changed as provided in display screen 180 shown in FIG. 7. The setting changes include a temperature scale field 182, a color scale field 184, a visual image field 186, and a live image field 189. The doctor can exit the display screen 180 by selecting the quit field 189.

Still referring to the flow diagram 100, when the thermal image 172 is stored within the remote storage device 60 at Block 130, the thermal analyzer 70 may be instructed to compare the thermal image 172 to the database of thermal images 72.

The thermal analyzer 70 may be configured to use machine learning to give the doctor statistical probabilities of certain disease states based on a thermal pattern within the thermal image 172. In the thermal image 172 of the patient's right posterior calf, the thermal analyzer 70 analyzes to see how much red is in the thermal image. This may be suggestive of venous insufficiency, and the thermal analyzer 70 then provides a statement such as "this area has a 95% likelihood of having venous insufficiency."

The thermal analyzer 70 is advantageously configured to take advantage that there is a unique situation in venous disease where there are incompetent superficial veins, i.e., where the valves have failed. In legs with normal veins, for example, blood that fills the superficial veins is collected from the capillaries of the skin and subcutaneous fat.

Since the blood has come from the skin capillary network which acts as a heat exchanger, the temperature of blood filling the superficial veins is at the same temperature as the skin, and flows from distal to proximal and from superficial to deep.

As there is no thermal differential the veins are indistinguishable from the skin on thermal imaging. In contrast, where valves have become incompetent blood flows in the opposite direction, flowing from deep to superficial and from proximal to distal. In this instance blood refluxing from deep is at a core temperature of approximately 37° C., when it refluxes and fills the superficial veins the heat conducts to the skin. Consequently, an area overlying the varicose tributary is hotter than the typical skin temperature of around 30° C.

The sensitivity of thermal imaging may be as good as 0.1° C. This makes it easier to identify the hot areas. The hot areas are of course always losing heat energy, but as blood refluxes continuously during standing and activity this heat is replenished, and will remain hotter for a period after an individual is recumbent when reflux ceases.

Thus, a thermal image of the leg will show only veins with reflux and therefore failed valves, as hot areas that are linear in nature and serpiginous the highest temperature follows the course of the vein. This pattern may also be seen in arteriovenous fistula but these are rare and simply differentiated using ultrasound.

Thermal imaging does not identify incompetent trunk veins as they are deep to the deep fascia of the leg and have a uniform insulating subcutaneous layer. Thermal imaging thus uniquely demonstrates and differentiates legs with venous incompetence from normal limbs. Acquiring thermal images for venous disease does not require any preparation of the leg, is entirely non-invasive and very time efficient.

Figure 8:
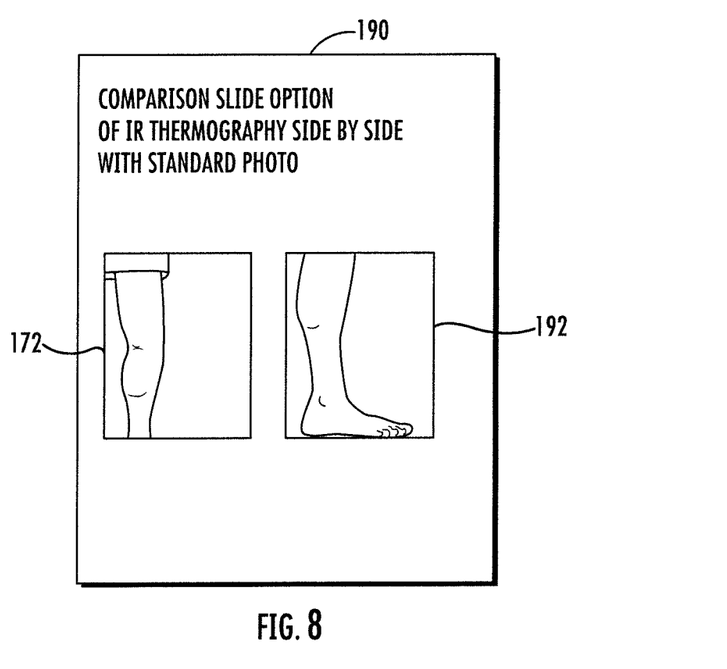

Referring back to operation of the clinical thermography application 52, a side by side comparison between a thermal image 172 and a standard photograph 192 may be performed as provided in display screen 190 shown in FIG. 8. The display screen 190 includes the thermal image 172 of the patient's right leg and a standard photograph 192 of the patient's right leg as provided by the camera 58. The thermal image 172 may be stored alongside the standard photograph 192 in the remote storage device 60.

Figure 9:
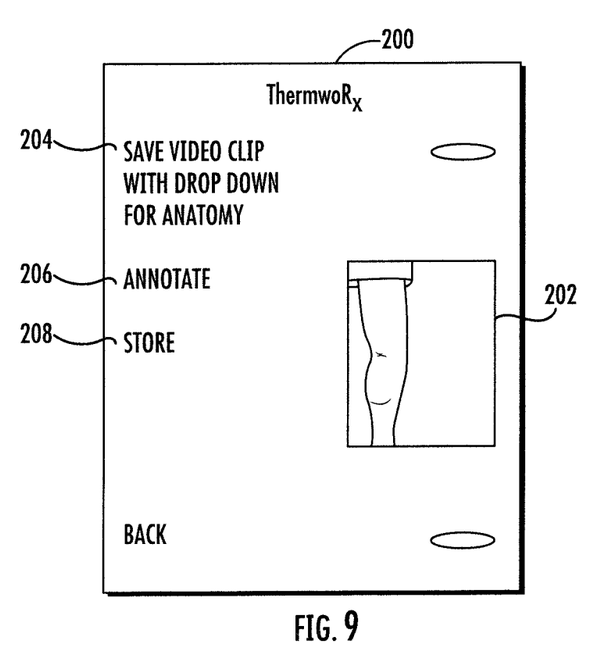

As an alternative to a thermal image, a thermal video clip 202 of the patient may be generated as provided in display screen 200 shown in FIG. 9. The same options available for a thermal image are available for a thermal video clip. The doctor has access to a save video clip field 204 for saving the thermal video clip 202. The thermal video clip 202 is saved within the memory 51 prior to being stored in the remote storage device 60.

The doctor has an option to annotate the thermal video clip 202 via the option to annotate field 206. If the doctor wants to store the annotated thermal video clip 202 within the remote storage device 60, then the store field 208 is selected. The thermal video clip 202 is stored within the cataloged patient thermal images 64. At Block 132 the doctor quits or exits the clinical based thermography application 52.

Figure 10:
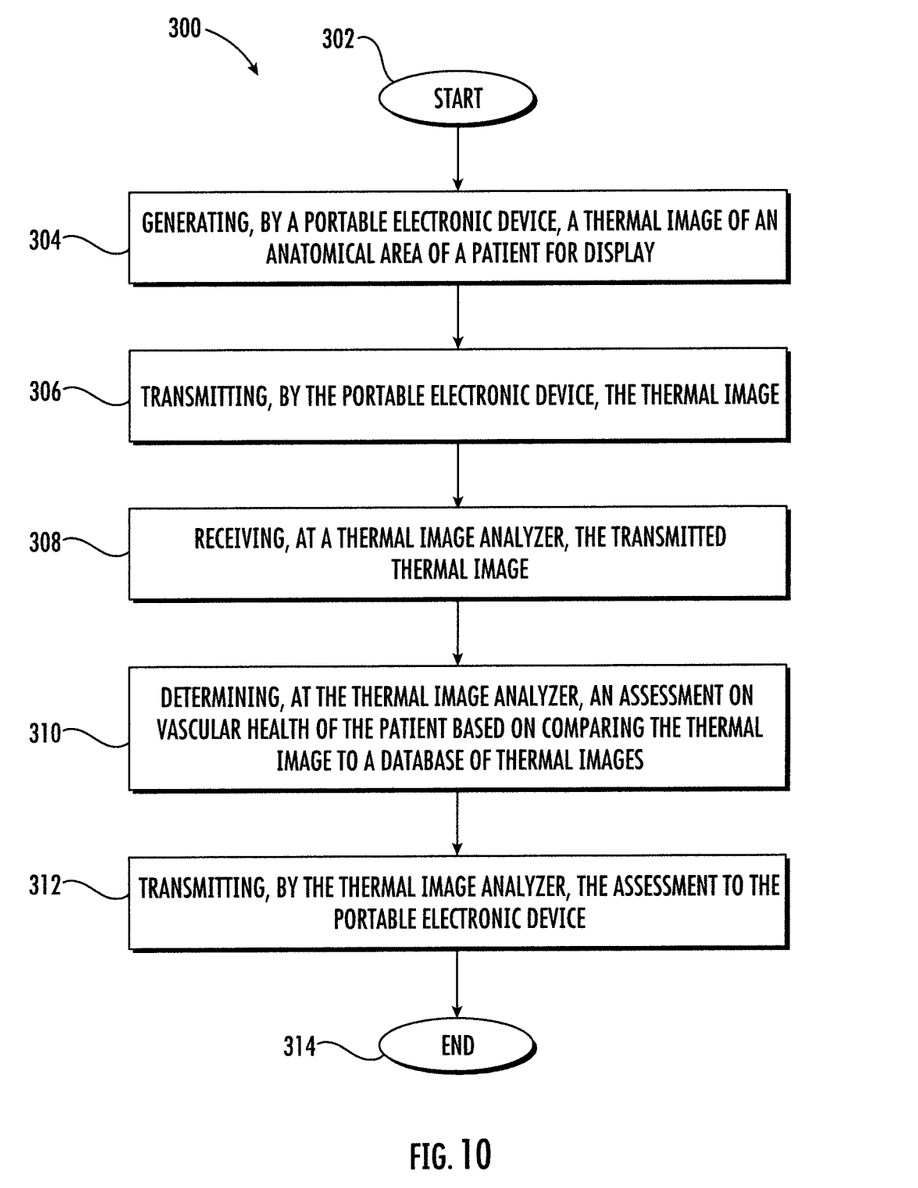
FIG. 10 is a flowchart illustrating a method for operating the infrared thermography system as illustrated in FIG. 1.

Referring now to FIG. 10, a flowchart 300 illustrating a method for operating the vascular thermography system 30 will be discussed. From the start (Block 302), the method includes generating, by the portable electronic device 40, a thermal image 172 of an anatomical area of a patient for display at Block 304. The portable electronic device 40 transmits the thermal image at Block 306. The method further includes receiving, at a thermal image analyzer 70, the transmitted thermal image at Block 308. The thermal image analyzer 70 determines an assessment on vascular health of the patient based on comparing the thermal image 174 to a database of thermal images 72 at Block 310. The thermal image analyzer 70 then transmits the assessment to the portable electronic device 40 at Block 312. The method ends at Block 314.

Figure 11:
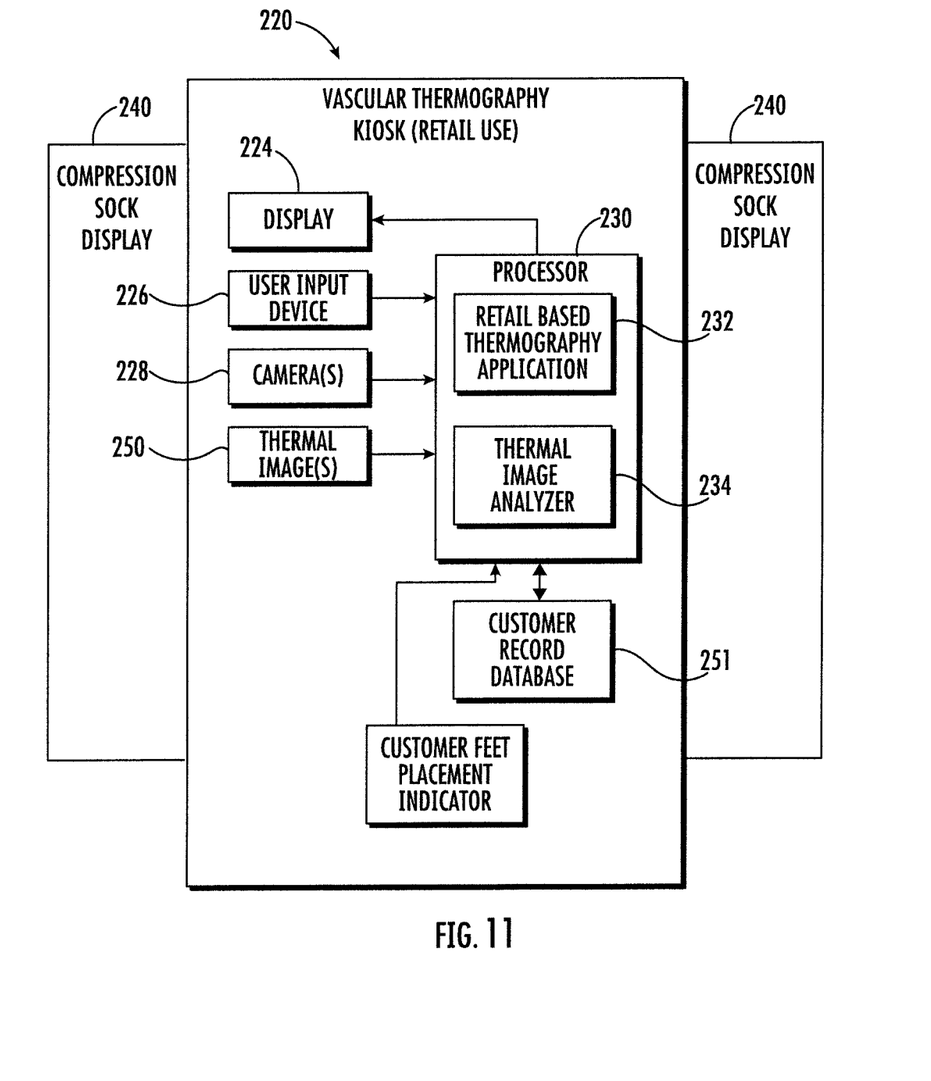
FIG. 11 is a block diagram of a retail based infrared thermography system in accordance with the disclosure.

Referring now to FIG. 11 a retail based vascular thermography kiosk 220 will be discussed. The vascular thermography kiosk 220 may be placed in shopping malls or stores, for example, and is configured to assess the vascular health of a customer's legs so as to recommend appropriately sized compression socks as necessary.

The vascular thermography kiosk 220 includes a housing 222, and one or more compression sock displays 240 attached to sides of the housing 222. The housing 222 carries a display 224, a user input device 226, a processor 230, at least one camera 228, at least one thermal imager 250, and a customer record database 251. The vascular thermography kiosk 220 further includes a customer feet placement indicator 252.

The customer feet placement indicator 252 allows a customer to stand on foot patterns that are in alignment with the thermal imager 250 and with the camera 228. When the system has a fixed thermal imager 250, the customer moves their feet to present the correct aspect to the thermal imager 250. The placement of the feet is guided by foot prints on the floor placed at an optimal distance from the fixed camera 228.

The thermal imager 250 generates one or more thermal images of the customer's legs, and the camera 228 also takes one or more picture of the customer's legs. The thermal imager 250 may be movable following a specific pattern to capture the relevant thermal images. Alternatively, there may be multiple thermal imagers 250 thereby avoiding the need for moving parts. The customer's legs are either bare or have tight clothing in contact with the skin, such as socks or stockings.

The thermal images may be displayed on the display 224 for customer viewing. Alternatively, the thermal images may be sent by internet to the customer and/or to a central location for storage and cataloging and review.

The thermal image will be processed to accentuate the hot vein pattern and may or may not subtract areas of normal heat, such as the anterior tibia area and popliteal fossa. The retail based thermography application 232 may further cooperate with the thermal imager 250 for setting a standard temperature scale and color pallet so that all images are comparable and consistent.

The thermal images and the photographs of the customer's legs may be stored photos in a customer record database 251. Execution of the retail based thermography application 232 by the processor 230 provides display prompts on the display 224. The display prompts require the customer answering a series of clinical questions. For example, these questions may include the following: do you have leg swelling Y/N, do you have leg cramps Y/N, etc.

The customer's answers to the questions, along with the thermal image and photograph of the customer's legs are used by the thermal image analyzer 234 to give the customer suggestions regarding their venous health and whether or not certain types of compression socks might be most useful for the customer.

The thermal image analyzer 234 may be included within the processor 230 as shown, or may be a separate processor operating in coordination with the processor 230. In other embodiments, the thermal image analyzer 234 may be cloud based wherein the vascular thermography kiosk 220 then communicates with through the internet. The thermal image analyzer 234 may be configured to use machine learning to provide statistical probabilities of certain disease states based on the thermal patterns of the customer's thermal image. The thermal image analyzer 234 will apply the algorithms to determine for each leg a) are the leg vein normal or abnormal, and b) are compression garments indicated.

Operation of the retail based thermography application 232 allows the processor 230 to determine length and diameter of the customer's legs and thus determine which size of compression stocking is most appropriate. The vascular thermography kiosk 220 includes compression sock displays 240 for purchase based on the results of the analyses performed by the thermal image analyzer 234.

As discussed above, the retail based vascular thermography kiosk 220 is a free standing autonomous system capable of deployment in public. The retail based vascular thermography kiosk 220 catalogs and stores customers' thermal images, and predicts the need for compression garments.

The retail based vascular thermography kiosk 220 is capable of producing a comprehensive map of a customer's incompetent venous circulation, and is capable of differentiating 'normal' areas of skin that are normally hotter than the general skin surface and disregarding them. The retail based vascular thermography kiosk 220 can in general determine normal from abnormal limbs (with regard to veins).

The thermal image analyzers 70, 234 may be based on artificial intelligence and machine learning. Veins of the leg, for example, are distributed in certain patterns and when they fail they do so in a variable recognizable number of patterns of varicose veins. Thermal imaging can detect these veins as broad areas of increased temperature above background.

The peak temperatures tend to follow the line of the vein which has a convoluted but linear form. Other areas of elevated temperature form a much more fixed pattern such as the area in the shin where the tibial bone is immediately beneath the skin, or behind the knee (the popliteal fossa, where subcutaneous fat is thinner).

In both these cases they do not create a linear pattern and so an algorithm can be developed to improve the specificity of the venous map by following the lines of maximum temperature and subtraction of area of diffuse high temperature. In this way a simplified but more accurate vein map can be created.

Knowledge of the absolute temperature range is also important. Body core temperature is 37° C., typical leg temperature of normal skin in the thigh at room temperature 20° C. is between 28-32° C. Blood that issues from the deep is at or close to body temperature while blood that is in normal superficial veins is at the temperature of the skin.

The skin capillaries act as a very efficient heat exchanger and so the arterial blood which arrives to feed the skin is cooled imparting its heat to the skin before being collected into the veins by which time there is little or no temperature difference. This makes normal veins invisible to thermal imaging, as there is no temperature gradient between skin and vein.

In contrast to varicose veins, vein valves have failed and permit blood (when the patient is standing) to reflux to fill veins immediately beneath the skin (varicose veins) at close to core temperature with little insulating fat and so heat the skin over the vein to a temperature greater than the surrounding skin. This is easily within the discriminatory range of the thermal imaging camera. Controlling the temperature range of the thermal imager to between 28-38° C., or more preferably 30-36° C., improves sensitivity and specificity of vein detection.

Many modifications and other embodiments will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included within the scope of the appended claims.

That which is claimed:

1. A vascular thermography system comprising:
    at least one portable electronic device comprising:
        a thermal imager configured to generate a thermal image of an anatomical area of a patient,
        a display,
        a processor configured to display the thermal image on said display, and
        a transceiver coupled to said processor and configured to transmit the thermal image; and
    a thermal image analyzer configured to perform the following:
        receive the thermal image from said at least one portable electronic device,
        use machine learning to determine an assessment on venous insufficiency of the patient based on comparing the thermal image to a database of thermal images, and
        transmit the assessment in real-time to said at least one portable electronic device.

2. The vascular thermography system according to claim 1 further comprising a remote storage device associated with said thermal image analyzer, said remote storage device configured to store a patient list and cataloged thermal images of patients on the patient list; and wherein said processor is further configured to execute a clinical thermography application to perform the following:
    display a login screen; and
    display vein scan settings based on a user of the at least one portable electronic device logging in, with the vein scan settings including at least one of the following:
        a live view setting allowing the user to immediately examine a patient,
        a new patient setting for the user to add a new patient to the patient list, and
        an existing patient setting for the user to retrieve an existing patient from the patient list.

3. The vascular thermography system according to claim 2 wherein said processor is further configured to perform the following based on execution of the clinical thermography application:
    display a drop down list of anatomical areas so the user can select one of the anatomical areas corresponding to the anatomical area being displayed in the thermal image; and
    store the thermal image with the user-selected anatomical area in the cataloged thermal images at said remote storage device.

4. The vascular thermography system according to claim 1 wherein said thermal image analyzer is cloud-based.

5. The vascular thermography system according to claim 1 wherein communications between said at least one portable electronic device and said thermal image analyzer is encrypted.

6. The vascular thermography system according to claim 1 wherein the database of thermal images comprises a plurality of thermal patterns corresponding to a range of venous insufficiency conditions, and wherein said thermal image analyzer is further configured to compare a thermal pattern within the thermal image to the plurality of thermal patterns in the database of thermal images.

7. The vascular thermography system according to claim 6 wherein the assessment on venous insufficiency of the patient includes statistical probabilities of certain disease states based on the thermal pattern within the thermal image.

8. The vascular thermography system according to claim 1 wherein said thermal image analyzer is further configured to use machine learning to determine the assessment on venous insufficiency of the patient.

9. The vascular thermography system according to claim 1 wherein said at least one portable electronic device further comprises:
    an external interface coupled to said processor; and
    a housing configured to carry said display, said processor, said transceiver, and said external interface;
    with said thermal imager being external said housing and removeably coupled to said external interface.

10. The vascular thermography system according to claim 1 wherein said at least one portable electronic device further comprises a camera configured to take a photograph of the same anatomical area as being displayed in the thermal image; and wherein said processor is further configured to display in a side-by-side comparison the thermal image and the photograph of the same anatomical area.

11. A vascular thermography system comprising:
    at least one portable electronic device comprising:
        a thermal imager configured to generate a thermal image of an anatomical area of a patient,
        a display,
        a transceiver, and a processor coupled to said thermal imager, said display, and said transceiver, and configured to execute a clinical thermography application to perform the following:
display the thermal image, display a drop down list of anatomical areas so the user can select one of the anatomical areas corresponding to the anatomical area being displayed in the thermal image, and
transmit the labeled thermal image;
a remote storage device configured to store the labeled thermal image as a cataloged thermal image of the patient; and
a thermal image analyzer associated with said remote storage device and configured to perform the following:
receive the cataloged thermal image from said remote storage device,
use machine learning to determine an assessment on venous insufficiency of the patient based on comparing the thermal image to a database of thermal images, and
transmit the assessment in real-time to said at least one portable electronic device.

12. The vascular thermography system according to claim 11 wherein said remote storage device is further configured to store a patient list and cataloged thermal images of patients on the patient list; and wherein said processor is further configured to perform the following based on execution of the clinical thermography application:
display a login screen; and
display vein scan settings based on a user of
the at least one portable electronic device logging in, with the vein scan settings including at least one of the following:
a live view setting allowing the user to immediately examine a patient,
a new patient setting for the user to add a new patient to the patient list, and
an existing patient setting for the user to retrieve an existing patient from the patient list.

13. The vascular thermography system according to claim 11 wherein said thermal image analyzer and said remote storage device are cloud-based.

14. The vascular thermography system according to claim 11 wherein communications between said at least one portable electronic device and said remote storage device and said thermal image analyzer is encrypted.

15. The vascular thermography system according to claim 11 wherein the database of thermal images comprises a plurality of thermal patterns corresponding to a range of venous insufficiency conditions, and wherein said thermal image analyzer is further configured to compare a thermal pattern within the cataloged thermal image to the plurality of thermal patterns in the database of thermal images.

16. The vascular thermography system according to claim 15 wherein the assessment on venous insufficiency of the patient includes statistical probabilities of certain disease states based on the thermal pattern within the cataloged thermal image.

17. A method for operating a vascular thermography system comprising at least one portable electronic device and a thermal image analyzer, with the at least one portable electronic device comprising a thermal imager, a display, a transceiver, and a processor coupled to the thermal imager, the display, and the transceiver, the method comprising:
operating the at least one portable electronic device to perform the following:
generating a thermal image of an anatomical area of a patient for display, and
transmitting the thermal image to the thermal image analyzer; and
operating the thermal image analyzer to perform the following:
receiving the thermal image from the at least one portable electronic device;
using machine learning in determining an assessment on venous insufficiency of the patient based on comparing the thermal image to a database of thermal images, and
transmitting the assessment in real-time to the at least one portable electronic device.

18. The method according to claim 17 wherein the vascular thermography system further comprises a remote storage device associated with the thermal image analyzer, with the remote storage device configured to store a patient list and cataloged thermal images of patients on the patient list; and wherein the at least one portable electronic device is further configured to execute a clinical thermography application to perform the following:
displaying a login screen; and
displaying vein scan settings based on a user of
the at least one portable electronic device logging in, with the vein scan settings including at least one of the following:
a live view setting allowing the user to immediately examine a patient,
a new patient setting for the user to add a new patient to the patient list, and
an existing patient setting for the user to retrieve an existing patient from the patient list.

19. The method according to claim 18 wherein the at least one portable electronic device is further configured to perform the following based on execution of the clinical thermography application:
displaying a drop down list of anatomical areas so the user can select one of the anatomical areas corresponding to the anatomical area being displayed in the thermal image; and
storing the thermal image with the user-selected anatomical area in the cataloged thermal images at the remote storage device.

20. The method according to claim 17 wherein the thermal image analyzer and the remote storage device are cloud-based.

* * * * *